(12) United States Patent
Malewicz et al.

(10) Patent No.: US 8,479,380 B2
(45) Date of Patent: Jul. 9, 2013

(54) CRIMPING DEVICE AND METHOD OF USE (75) Inventors: Andrzej M. Malewicz, Minneapolis, MN (US); Matthew W. Weston, Little Canada, MN (US)

(73) Assignee: Medtronic 3F Therapeutics, Inc., Irvine, CA (US)

( * ) Notice: Subject to any disclaimer, the term of this patent is extended or adjusted under 35 U.S.C. 154(b) by 315 days.

(21) Appl. No.: 12/870,593

(22) Filed: Aug. 27, 2010

(65) Prior Publication Data

US 2011/0056064 A1 Mar. 10, 2011

Related U.S. Application Data

(60) Provisional application No. 61/238,063, filed on Aug. 28, 2009, provisional application No. 61/287,030, filed on Dec. 16, 2009, provisional application No. 61/322,480, filed on Apr. 9, 2010.

(51) Int. Cl.
*B23P 19/00* (2006.01)

(52) U.S. Cl.
USPC .......................................................... 29/760

(58) Field of Classification Search
USPC ................... 29/446, 760, 515, 525, 282, 237, 29/751, 235, 508; 604/159, 510; 606/1; 623/1.12

See application file for complete search history.

(56) References Cited

U.S. PATENT DOCUMENTS

| | | | |
|---|---|---|---|
| 5,626,604 | A | 5/1997 | Cottone, Jr. |
| 5,738,674 | A | 4/1998 | Williams et al. |
| 5,911,752 | A | 6/1999 | Dustrude et al. |
| 6,082,990 | A | 7/2000 | Jackson et al. |
| 6,141,855 | A | 11/2000 | Morales |
| 6,167,605 | B1 | 1/2001 | Morales |
| 6,240,615 | B1 | 6/2001 | Kimes et al. |
| 7,290,322 | B2 | 11/2007 | Cai et al. |
| 7,530,253 | B2 | 5/2009 | Spenser et al. |
| 7,895,876 | B2 | 3/2011 | Spenser et al. |
| 2002/0138966 | A1 | 10/2002 | Motsenbocker |
| 2003/0065381 | A1 | 4/2003 | Solar et al. |
| 2005/0143752 | A1 | 6/2005 | Schwager et al. |
| 2009/0054976 | A1 | 2/2009 | Tuval et al. |

*Primary Examiner* — John C Hong (57) ABSTRACT

A crimping tool for crimping a stented heart valve comprises a housing having a front wall and a back wall, a compression assembly disposed between the front wall and the back wall and including a stent receiving chamber therewithin for receiving a stented heart valve, and a delivery device holder slidably coupled to the front wall of the housing. The compression assembly is movable between an uncrimped position and a crimped position to reduce the diameter of the stented heart valve.

10 Claims, 13 Drawing Sheets

CRIMPING DEVICE AND METHOD OF USE

CROSS-REFERENCE TO RELATED APPLICATIONS

This application claims priority under 35 U.S.C. §119(e)(1) to U.S. Provisional Patent Application Ser. Nos. 61/238,063, filed Aug. 28, 2009; 61/287,030, filed Dec. 16, 2009; and 61/322,480, filed Apr. 9, 2010; the entire teachings of each of which are incorporated herein by reference.

FIELD

The present disclosure is generally directed to a tool used to decrease the diameter of an element. More particularly, the present disclosure is directed to a crimping tool and method for radially compressing a stent from a first diameter to a reduced second diameter.

BACKGROUND

Heart valve replacement is required when a patient's heart valve becomes diseased or damaged. Surgically implanted heart valve prostheses have extended the life expectancy of many patients with defective heart valves. Such prostheses can be either mechanical or biological (tissue valves), stented or stentless, and may be implanted into an aortic, mitral, tricuspid, or pulmonary position.

During this surgical procedure, the heart is typically stopped and the patient attached to a heart/lung bypass machine that pumps and oxygenates the patient's blood. The longer a patient is required to rely on the artificial heart/lung bypass machine to maintain vital functions, the greater the stress on the patient. There is consequently a need to simplify the surgical implantation of a heart valve prosthesis into the implantation annulus in order to minimize both the length of surgery and the amount of time spent on heart/lung bypass.

Stented heart valves made from flexible material or from materials that exhibit shape memory characteristics promise less complicated and faster valve implantation procedures. The stents supporting the heart valves are generally cylindrical in shape and are structured to be crimped so as to reduce their size for delivery to a target site. The crimped stent and attached heart valve may be delivered to the target site with any suitable means, such as a catheter or the like. Once positioned in the desired location, the stent may be re-expanded to secure the heart valve in place by exerting radial forces against the internal walls of the implantation annulus. The stents may be either self-expanding or non self-expanding. Self-expanding stents may be formed from any suitable shape memory material, such as Nitinol. Non self-expanding stents are typically expanded via an inflation means or mechanical expansion means. Stented heart valves are sometimes referred to as suture-less valves since they may be implanted and secured into the annulus without the use of sutures.

As appreciated by those skilled in the art, it is desirable to crimp the stent in a substantially uniform manner to minimize the variation in pressures applied to the stent. Such pressure variations may lead to deformation of the stent, which may reduce the ability of the stent to securely maintain the heart valve at the target location. Thus, if a stent is crimped in a non-uniform manner, it is typically either re-crimped or thrown away. Re-crimping of stents is not desirable because the repeated application of force on the stent may cause fatigue or weakening of the stent structure. Disposing of poorly crimped stents is also not desirable due to the increased costs associated with the waste. This is especially true with stented heart valves because the stent and the heart valve are attached together and must be disposed of as a single unit.

Therefore, what is needed is an improved device and method for radially crimping a stent from a first diameter to a reduced second diameter. What is further needed is an improved device and method that provides substantially uniform crimping, minimizes unnecessary waste, and allows a crimped stent to be easily loaded into a delivery device.

SUMMARY

The present disclosure addresses the foregoing needs by providing a novel crimping tool for crimping a stented heart valve that includes a housing having a front wall and a back wall, a compression assembly disposed between the front wall and the back wall and including a stent receiving chamber therewithin for receiving a stented heart valve, and a delivery device holder slidably coupled to the front wall of the housing. The compression assembly is movable between an uncrimped position and a crimped position to reduce the diameter of the stented heart valve.

DETAILED DESCRIPTION

The present disclosure is generally directed to a crimping tool and associated method for reducing the size of an element, such as by decreasing the diameter of an element from a first diameter to a decreased second diameter. One use of the crimping tool is for crimping a radially compressible stent or stented heart valve in preparation for deployment within a patient. However, the crimping tool may be used for reducing the size of numerous other types of compressible elements as will be appreciated by those skilled in the art. Thus, the following disclosure focuses on reducing the size of radially compressible stents merely for purposes of example and not limitation.

In operation, the crimping tool is structured to exert radially compressive forces on the stent in order to reduce the size of the stent. In one embodiment, the crimping tool is operable to radially compress a stent to approximately 50% of its original size. However, crimping tools may be provided that compress a stent to any fraction of its original size without departing from the intended scope of the present disclosure.

Figure 1:
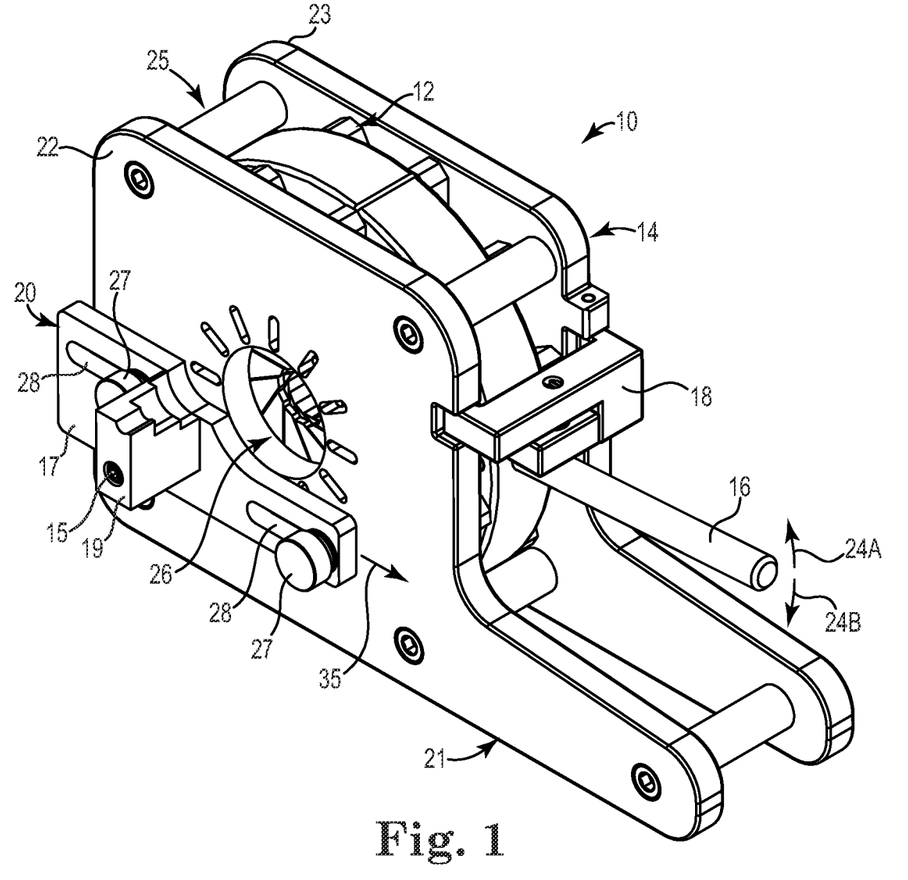
FIG. 1 is a perspective view of one exemplary embodiment of a crimping tool in accordance with the present disclosure.

FIG. 1 is a perspective view of one embodiment of a crimping tool 10 in accordance with the present disclosure. As illustrated in FIG. 1, the crimping tool 10 generally includes a compression assembly 12 disposed within a housing 14, an actuation lever 16, a lever lock 18, and a delivery device holder 20. The housing 14 includes an elongated base portion 21 that is sized and structured to provide sufficient support and stability to the crimping tool 10 during use. As will be appreciated by those skilled in the art, the base portion 21 of the housing 14 may be positioned on or attached to a table or other support surface during use of the crimping tool 10. In alternative embodiments, the base portion 21 may be a separate structure that is coupled to the housing 14 instead of being formed integral therewith.

As illustrated in FIG. 1, the housing 14 of the crimping tool 10 includes a front wall or plate 22 and a back wall or plate 23 coupled together in a spaced apart relationship so as to define an opening 25 therebetween. The compression assembly 12 is disposed between the front plate 22 and the back plate 23 and is operably coupled to the actuation lever 16 such that the actuation lever 16 extends through the opening 25. As will be discussed in further detail to follow, movement of the actuation lever in the directions indicated by arrows 24A and 24B controls movement of the compression assembly 12 between an uncrimped position and a crimped position, respectively. The actuation lever 16 of FIG. 1 is designed for manual operation by an operator, such as by grasping and moving the actuator 16 by hand. However, alternative embodiments of the crimping tool 10 may include actuation levers that are operated via alternative mechanical, electrical, hydraulic, electromechanical, or computer-controlled actuation means without departing from the intended scope of the present disclosure.

The housing 14 of the crimping tool 10 is described as being formed by two spaced apart plates that are coupled together so as to form an opening therebetween merely for purposes of example and not limitation. Thus, numerous other housing configurations may be used as will be appreciated by those skilled in the art. In one alternative embodiment, the housing 14 may instead be formed as a rear housing portion having a cavity that is structured to receive the compression assembly 12 and a cover plate that may be coupled to the rear housing portion such that the compression assembly 12 is substantially enclosed therein. Furthermore, the housing 14 may be constructed using any suitable materials including, but not limited to, various metals or plastics.

Although not a necessary component of the present disclosure, the lever lock 18 is hingedly coupled to the housing 14 and operable to lock the actuation lever 16 when the compression assembly 12 is in the crimped position. As illustrated in FIG. 1, the lever lock 18 "blocks" movement of the actuation lever 16 in the direction indicated by arrow 24A thereby preventing unintentional expansion of the compression assembly 12 and the (not shown) positioned therein from the crimped position back toward the uncrimped position. As discussed above, repeated cycles of compression and expansion of a stent may lead to fatigue or weakening of the stent structure. Thus, the lever lock 18 may be used to ensure that the stent is only crimped a single time prior to delivery to a patient.

The delivery device holder 20 is structured to engage a delivery device and align the delivery device with an access aperture 26 in the front plate 22 of the housing 14 that is sized to allow a stent (not shown) to be passed therethrough and into the compression assembly 12 for crimping. This alignment allows the crimped stent to be loaded into the delivery device for subsequent delivery to a patient. More particularly, as illustrated in FIG. 1 the delivery device holder 20 includes a sliding plate 17 having a seat member 19 that is structured to mate with or engage the delivery device. As will be appreciated by those skilled in the art, the structure and contour of the seat member 19 may vary depending upon the type of delivery device that is being supported. The sliding plate 17 and the seat member 19 are illustrated in FIG. 1 as separate components that are coupled together with a suitable fastening means such as a fastener 15. Alternatively, the sliding plate 17 and the seat member 19 may be formed as a single, integral unit.

The sliding plate 17 is slidably coupled to the front plate 22 of the housing 14 via at least one engagement member 27 positioned within a corresponding horizontal slot 28. The delivery device holder 20 is structured for movement in the direction indicated by arrow 35 from a first position as illustrated in FIG. 1 wherein the seat member 19 is not aligned with a center axis of the access aperture 26 to a second position wherein the seat member 19 is substantially aligned with the center axis of the access aperture 26. The range of movement of the delivery device holder 20 is determined by the length of the horizontal slot 28 in the sliding plate 17.

The delivery device holder 20 of FIG. 1 is illustrated as including two engagement members 27 and two corresponding horizontal slots 28 merely for purposes of example and not limitation. Those skilled in the art will appreciate that any number of engagement members and corresponding slots may be used without departing form the intended scope of the present disclosure.

Figure 2:
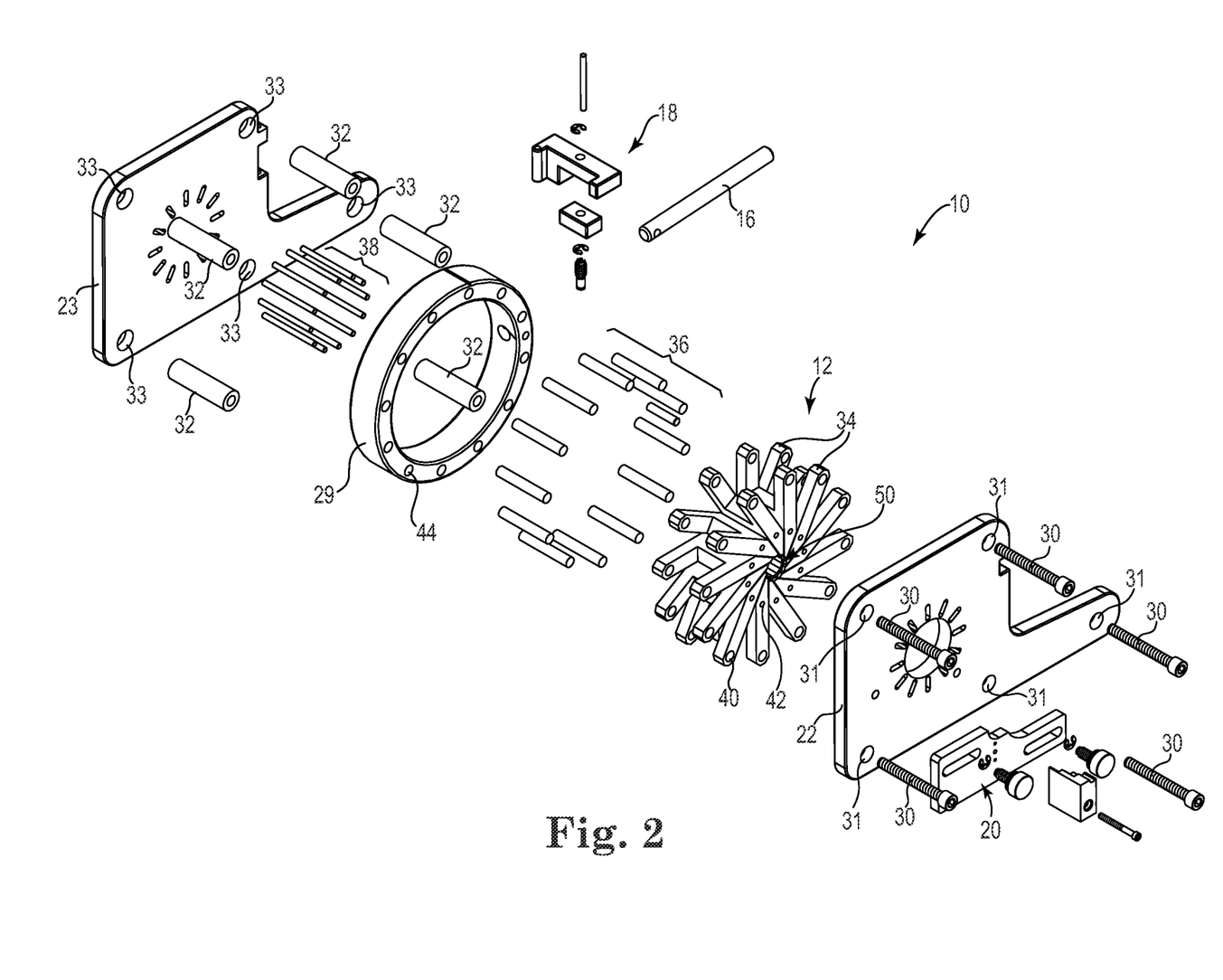
FIG. 2 is an exploded perspective view of the crimping tool of FIG. 1.

FIG. 2 is an exploded perspective view of the crimping tool 10 of FIG. 1. As illustrated in FIG. 2, the crimping tool 10 further includes a drive wheel 29 that, along with the compression assembly 12, is structured to be positioned between the front plate 22 and the back plate 23 of the housing 14. The drive wheel 29 is a generally cylindrical structure with an open center portion, thereby resembling a rim or ring member. The drive wheel 29 is rotatable with respect to the housing 14 and operably coupled to the compression assembly 12 to drive movement of the compression assembly 12 during the crimping process. As will be appreciated by those skilled in the art, the front plate 22 and the back plate 23 are spaced sufficiently apart when assembled (FIG. 1) such that the drive wheel 29 and attached compression assembly 12 may freely rotate therebetween. The actuation lever 16 is designed to operably engage the drive wheel 29 to initiate and control the movement of the drive wheel 29. As will be appreciated by those skilled in the art, the actuation lever 16 may be coupled to the drive wheel 29 in any suitable manner, or alternatively may be formed integral with the drive wheel 29.

With the crimping tool 10 illustrated in FIG. 2, the front plate 22 is attachable to the back plate 23 with a plurality of fasteners 30 that are structured to be passed though corresponding pluralities of apertures 31 in the front plate 22, elongate spacer elements 32 positioned between the front plate 22 and the back plate 23, and apertures 33 in the back plate 23. The fasteners 30 may have external threads that are structured to engage with internal threads of the apertures 31 in the front plate 22 and/or the apertures 33 in the back plate 23. As will be appreciated by those skilled in the art, numerous other means for attaching the front plate 22 to the back plate 23 of the housing 14 are contemplated and within the intended scope of the present disclosure including, but not limited to, rivets, welding, an adhesive, or the like. Thus, threaded fasteners are described and illustrated merely for purposes of example and not limitation.

As illustrated in FIG. 2, the compression assembly 12 includes a plurality of bars 34, a plurality of drive pins 36, and a plurality of guide pins 38. The drive pins 36 and guide pins 38 are preferably metallic and generally cylindrical in shape, although the pins may be constructed in various other shapes and from various other materials without departing from the intended scope of the present disclosure. Each of the bars 34 includes a generally cylindrical drive pin slot 40 structured to receive one of the drive pins 36 and a generally cylindrical guide pin slot 42 structured to receive one of the guide pins 38. The drive wheel 29 includes a plurality of generally cylindrical drive wheel slots 44 that are structured to receive the drive pins 36 to operably couple the drive wheel 29 to the plurality of bars 34 of the compression assembly 12. The drive pin slots 40 and/or the drive wheel slots 44 may be sized such that they have a diameter that is slightly larger than the diameter of the drive pins 36 to allow the bars 34 to rotate or pivot with respect to the drive wheel 29 as the drive wheel is rotated with the actuation lever 16. The guide pin slots 42 may be sized similar to the guide pins 38 such that a friction fit is formed therebetween, or alternatively the guide pin slots 42 may be sized larger than the guide pins 38 to allow for slight rotation of the distal end of the bars 34.

The crimping tool 10 is described and illustrated herein as including a single plurality of drive pins 36 and a single plurality of guide pins 38 merely for purposes of example and not limitation. In alternative embodiments, the compression assembly 12 may include a first plurality of drive pins structured to extend from the drive wheel slots 44 toward the front side of the bars 34 adjacent the front plate 22 and a second plurality of drive pins structured to extend from an opposite end of the drive wheel slots 44 toward the back side of the bars 34 adjacent the back plate 23. Similarly, the compression assembly 12 may include a first plurality of guide pins structured to extend from the guide pin slots 42 in the bars 34 toward the front plate 22 and a second plurality of guide pins structured to extend from an opposite end of the drive pin slots 42 in the bars 34 toward the back plate 23.

The drive wheel slots 44 may be substantially equally spaced around the circumference of the drive wheel 29. Furthermore, as illustrated in FIG. 2 the number of drive wheel slots 44 is equal to the number of bars 34 in the compression assembly 12. Thus, each bar 34 includes one drive pin slot 40, one guide pin slot 42, and is associated with one drive wheel slot 44 in the drive wheel 29. With embodiments in which the drive wheel slots 44 are equally spaced around the circumference of the drive wheel 29, the bars 34 are also equally spaced around the circumference of the drive wheel 29 in a spoke-like fashion.

As will be described in further detail to follow, the bars 34 are arranged to form a generally circular or polygonal chamber 50 that is structured to receive a stent (not shown) or other element to be crimped. With the stent positioned within the chamber 50, the internal dimensions of the chamber 50 may be reduced by manipulating the actuation lever 16 as previously discussed, thereby moving the compression assembly 12 from an uncrimped position to a crimped position. The extent to which the dimensions of the chamber 50 are reduced, and thus the amount of crimping, may be controlled by the position of the actuation lever 16. In the embodiment of the crimping tool 10 illustrated herein, the actuation lever 16 moves in a clockwise direction during the crimping process. However, those skilled in the art will appreciate that the compression assembly 12 may be modified such that the actuation lever 16 instead moves in a counter-clockwise direction during the crimping process.

Figure 3A:
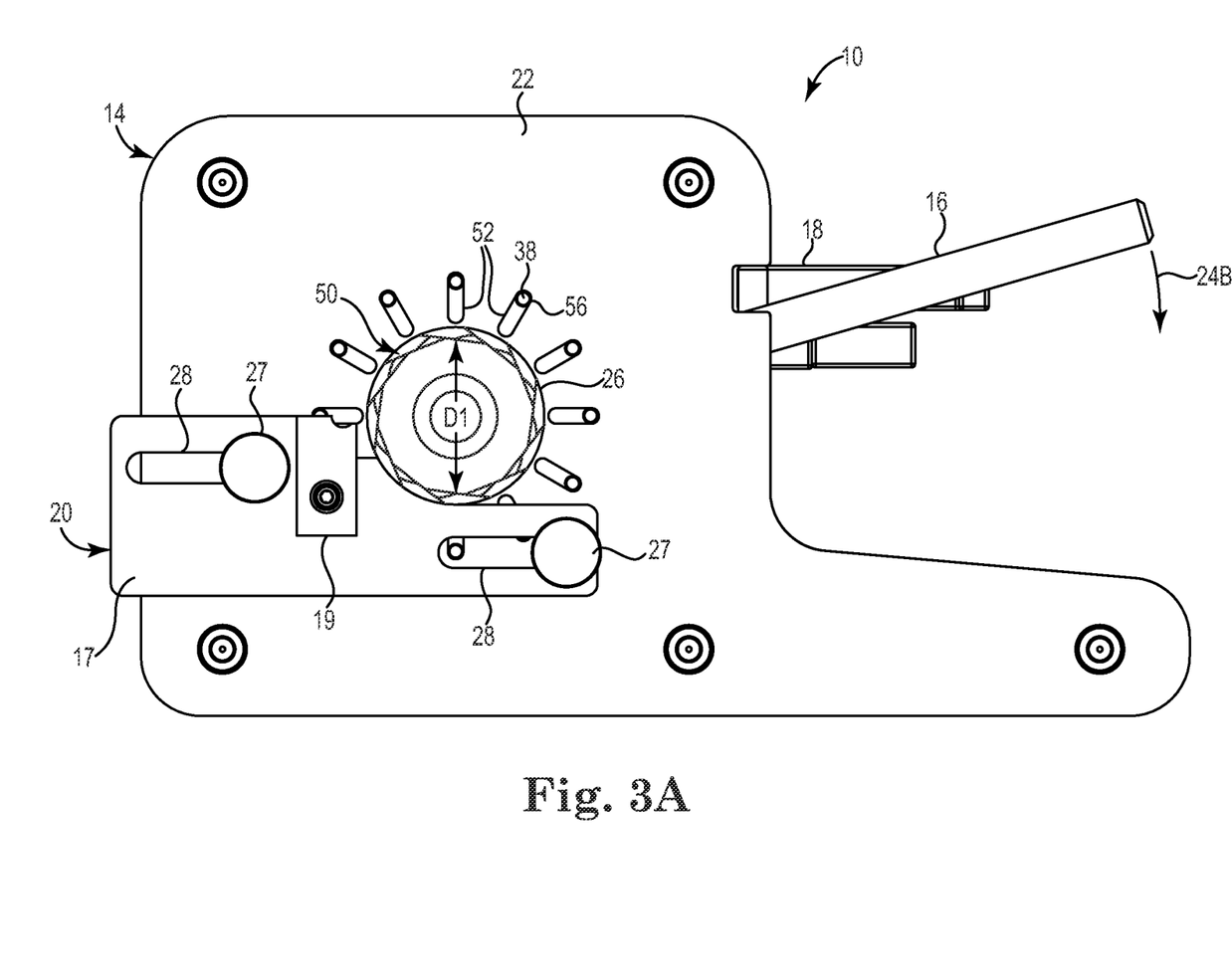
FIGS. 3A and 3B are front and back views, respectively, of the crimping tool of FIG. 1 illustrating a compression assembly in an uncrimped position.
Figure 3B:
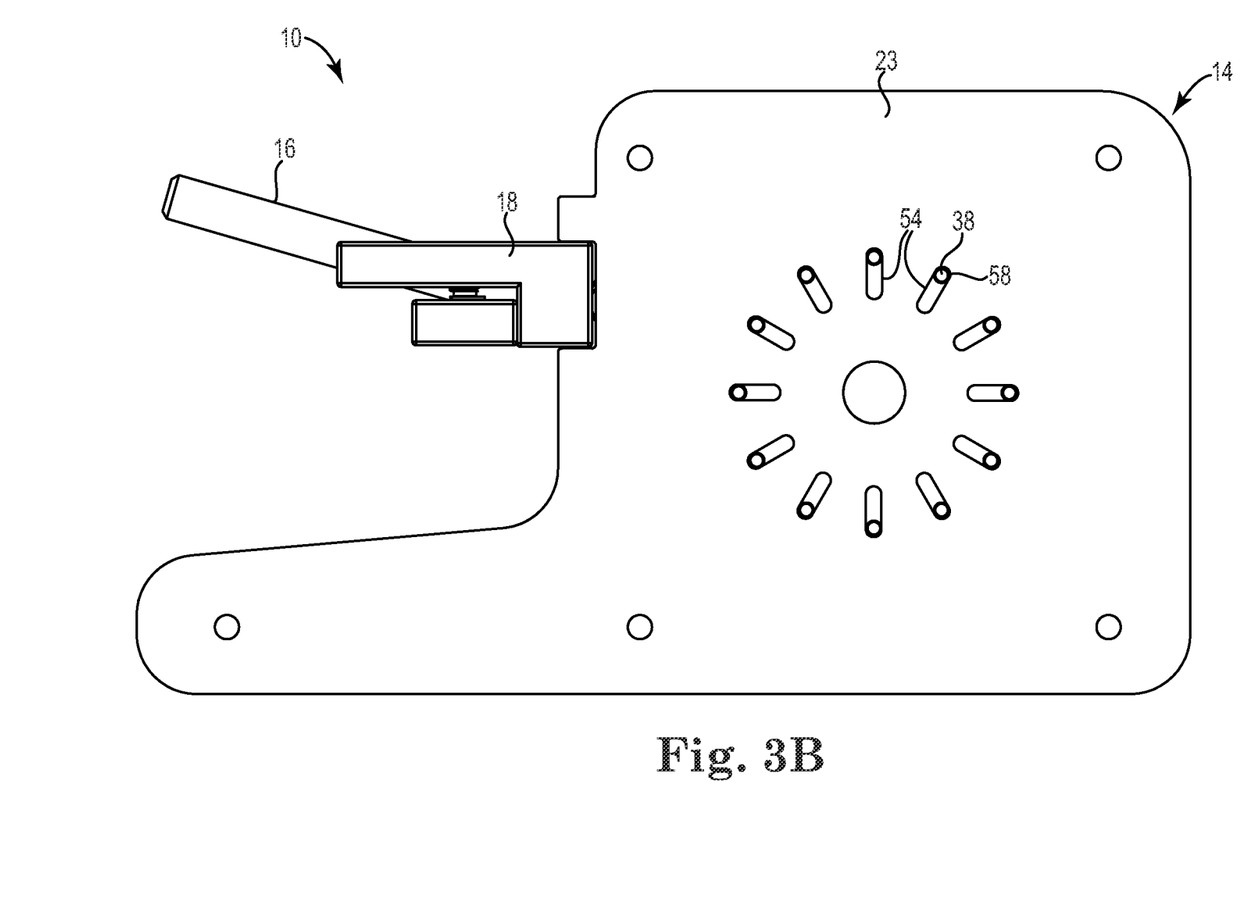

FIGS. 3A and 3B are front and back views, respectively, of the crimping tool 10 in accordance with the present disclosure. As illustrated in FIG. 3A, the front plate 22 of the housing 14 includes a first plurality of radially extending elongate slots 52. Similarly, as illustrated in FIG. 3B, the back plate 23 of the housing 14 includes a second plurality of radially extending elongate slots 54 that are aligned with the first plurality of elongate slots 52. When assembled, each of the guide pins 38 is structured to pass through a corresponding guide pin slot 42 in one of the bars 34 as previously discussed. Additionally, each of the guide pins 38 is designed with a length that is sufficient to allow a first end of the guide pin 38 to extend into a corresponding one of the elongate slots 52 in the front plate 22 and a second end of the guide pin 38 to extend into a corresponding one of the elongate slots 54 in the back plate 23. As will be appreciated by those skilled in the art, the elongate slots 52 and 54 are structured and sized to allow a predetermined amount of radial movement of the guide pins 38 and attached bars 34 during the crimping process to alter the dimensions of the chamber 50.

Figure 4A:
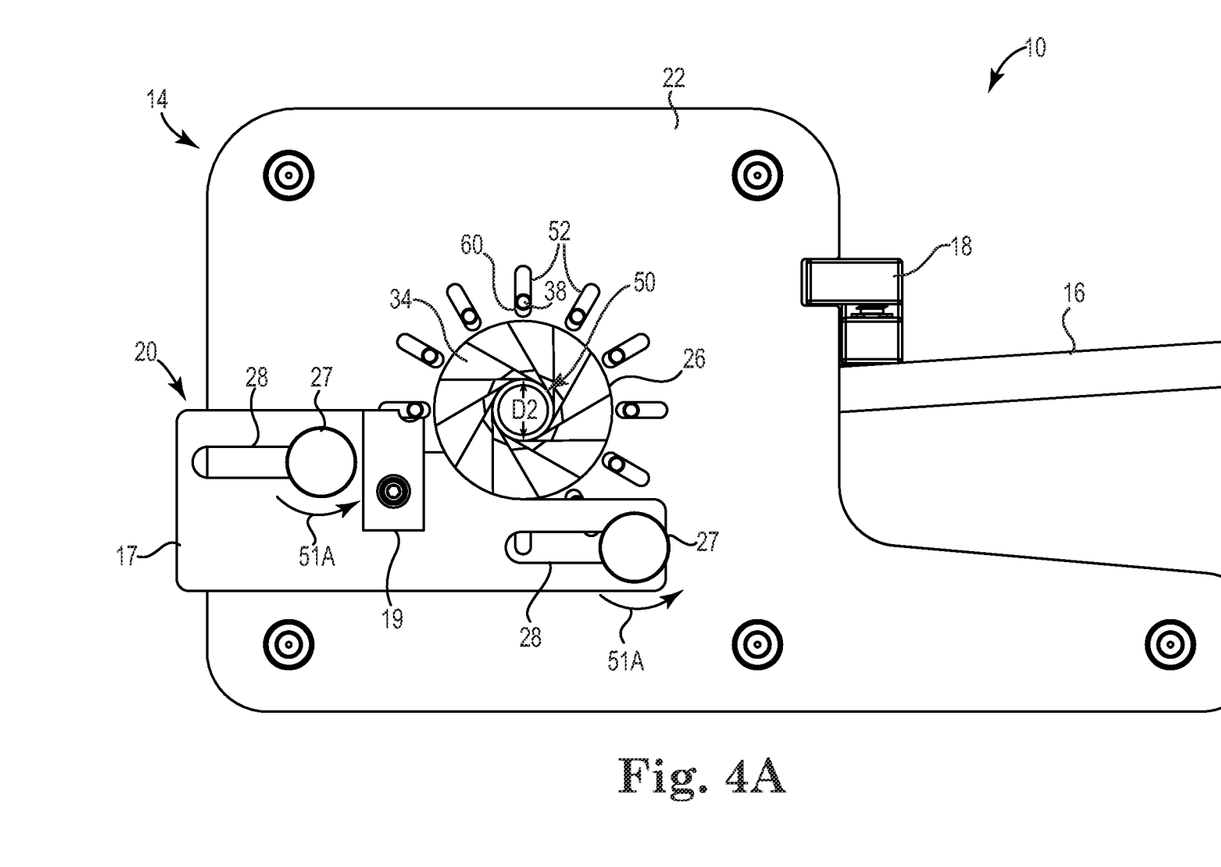
FIGS. 4A and 4B are front and back views, respectively, of the crimping tool of FIG. 1 illustrating the compression assembly in a crimped position.
Figure 4B:
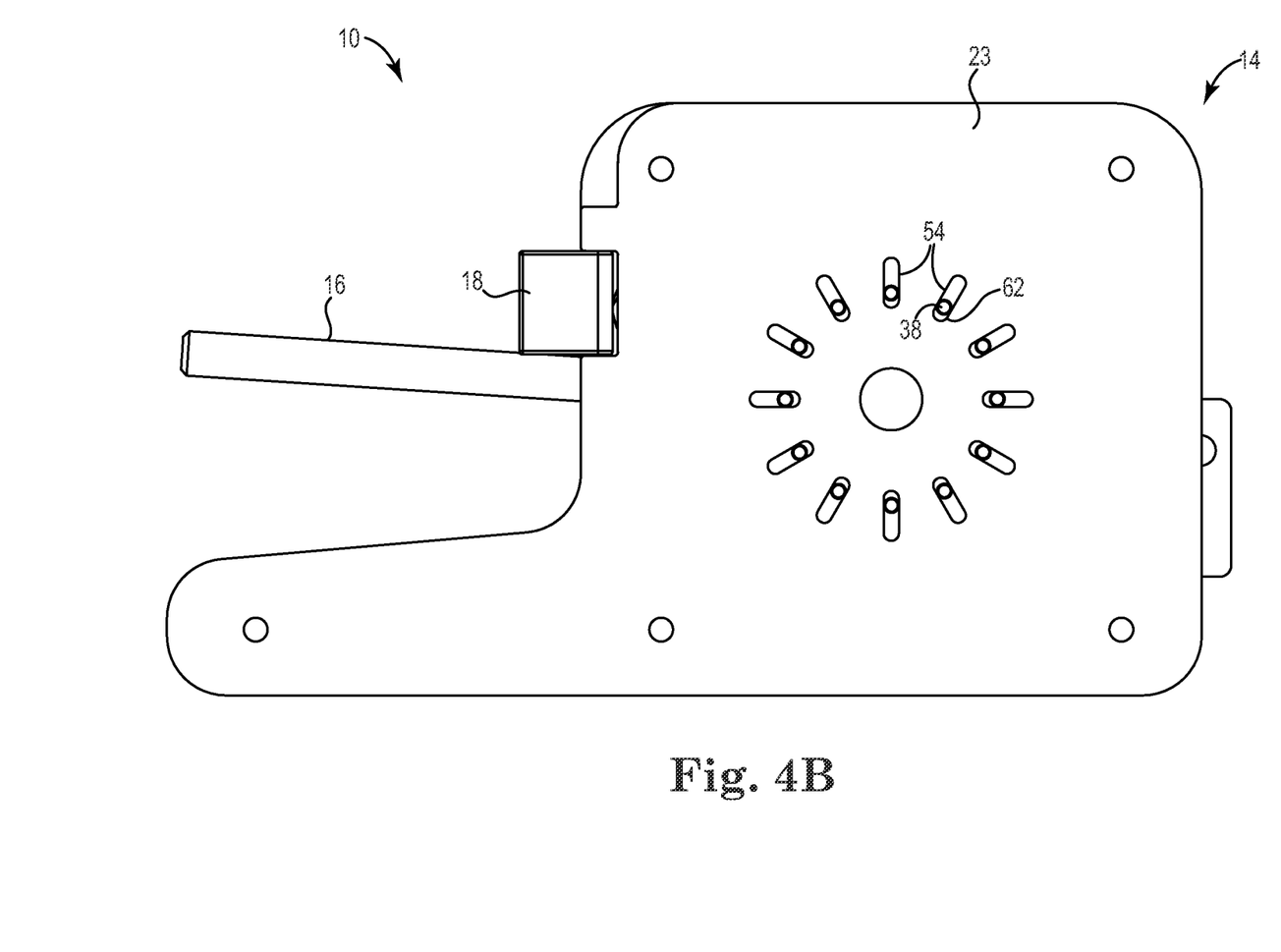

In the state of FIGS. 3A and 3B, the compression assembly 12 is in an "uncrimped" position. FIGS. 4A and 4B are front and back views, respectively, of the crimping tool 10 illustrating the compression assembly 12 in a "crimped" position. As will be appreciated by those skilled in the art, the uncrimped position of FIGS. 3A and 3B and the crimped position of FIGS. 4A and 4B represent the two endpoints of the crimping range. Depending upon the size of the stent and the amount of crimping that is desired, an operator may achieve a desirable amount of crimping without actuating the compression assembly 12 to the fully crimped position of FIGS. 4A and 4B.

With reference again to the uncrimped position of FIG. 3A, the chamber 50 is defined by a first internal dimension D1, which may approximately represent the diameter of a circle. When the chamber 50 is in the uncrimped position, each of the guide pins 38 is positioned substantially adjacent to a first end 56 of a corresponding elongate slot 52 in the front plate 22 as illustrated in FIG. 3A and a first end 58 of a corresponding elongate slot 54 in the back plate 23 as illustrated in FIG. 3B. In order to commence the crimping process to decrease the internal diameter D1 of the chamber 50, the operator may move the actuation lever 16 in the direction indicated by arrow 24B.

As illustrated in the crimped position of FIG. 4A, the chamber 50 is defined by a reduced second internal dimension D2, which may also approximately represent the diameter of a circle. As will be appreciated by those skilled in the art, a center axis of the chamber 50 corresponds with the center axis of the access aperture 26. When the chamber 50 is in the crimped position, each of the guide pins 38 is positioned substantially adjacent to a second end 60 of a corresponding elongate slot 52 in the front plate 22 as illustrated in FIG. 4A and a second end 62 of a corresponding elongate slot 54 in the back plate 23 as illustrated in FIG. 4B. As the chamber 50 contracts and becomes smaller, the internal surface defining the chamber 50 moves toward the center axis of the chamber 50 in a substantially uniform manner such that the chamber maintains a substantially circular configuration throughout the crimping process. This uniform compression is the result of the interaction between the bars 34, the drive pins 36, the guide pins 38, and the elongate slots 52 and 54 in the housing 14.

More specifically, during the crimping process, movement of the actuation lever 16 in the clockwise direction 24B causes the drive wheel 29 to also move in the clockwise direction. Because the bars 34 of the compression assembly 12 are operably coupled to the drive wheel 29 with the drive pins 36 at a proximal end, the proximal ends of the bars 34 are caused to rotate clockwise along with the drive wheel 29. As discussed above, in order to allow movement of the bars 34 relative to one another to adjust the size of the chamber 50, the drive pins 36, drive pin slots 40, and drive wheel slots 44 are sized such that the bars 34 are rotatable or pivotable with respect to the drive wheel 29 along an axis through the drive pins 36. However, the distal ends of the bars 34 are constrained from any substantial amount of rotation due to the engagement of the guide pins 38 with the elongate slots 52 in the front plate 22 and the elongate slots 54 in the back plate 23. As a result, the guide pins 38 are allowed to slide inward along the radially extending elongate guide slots 52 and 54 to reduce the internal diameter of the chamber 50.

As will be appreciated by those skilled in the art, any radially compressible stent having a diameter in the expanded state that is greater than D2 but less than D1 may be crimped with the crimping tool 10 of the present disclosure. Furthermore, the size of the chamber 50 in the uncrimped and crimped positions may be modified by changing, for example, the number, size, or shape of the bars 34 of the compression assembly 12.

As illustrated in FIGS. 3A and 4A, the delivery device holder 20 is located in the first position wherein the seat member 19 is not aligned with the center axis of the access aperture 26. Once the stent (not shown) or other device has been crimped within the chamber 50, the seat member 19 of the delivery device holder 20 may be substantially aligned with the center axis of the access aperture 26 by moving the sliding plate 17 to the position illustrated in FIG. 5. With the seat member 19 of the delivery device holder 20 substantially aligned with the center axis of the access aperture 26, the crimped stent may be easily loaded into the delivery device (not shown) for subsequent deployment within a patient.

Figure 5:
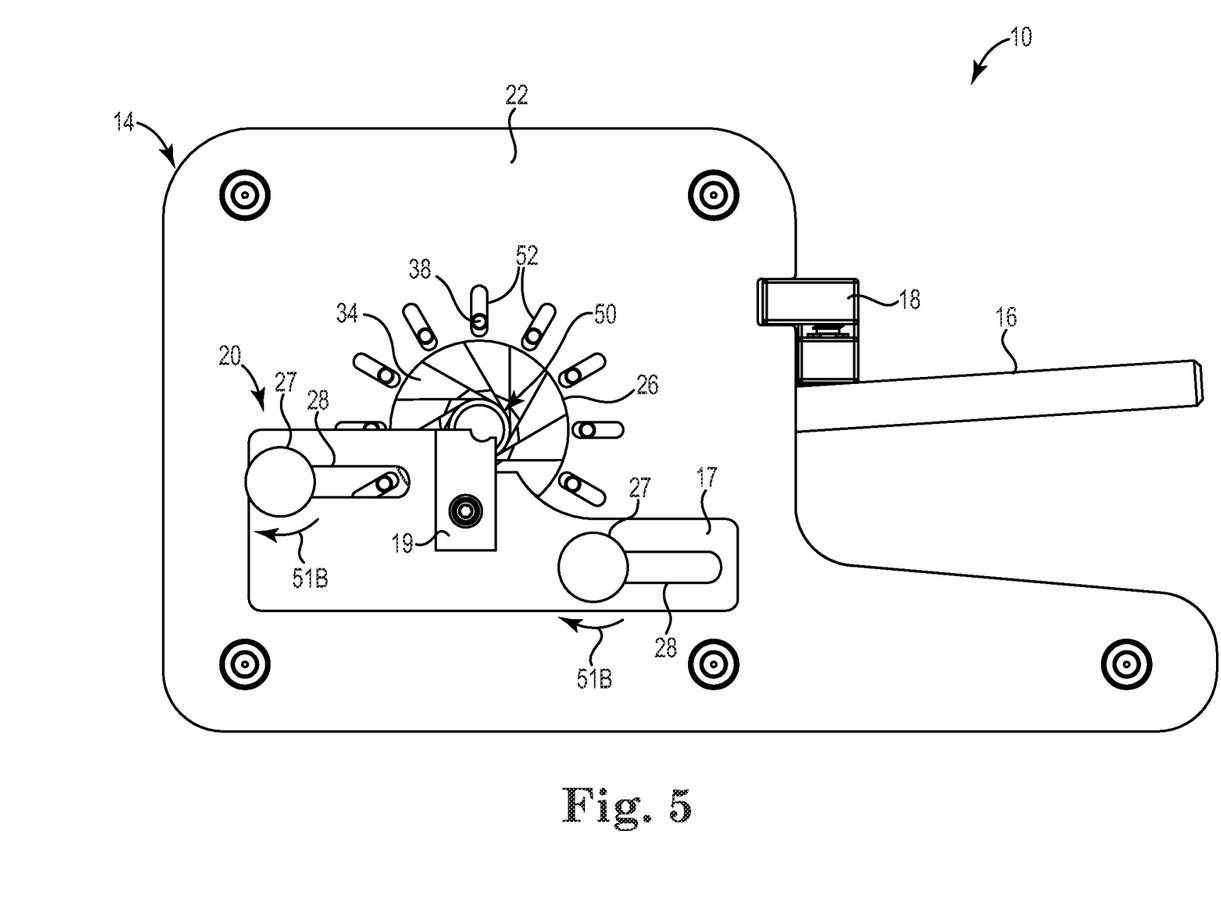
FIG. 5 is a front view of the crimping tool of FIG. 1 illustrating a delivery device holder having a seat member aligned with an access aperture of the crimping tool.

In the embodiment of the delivery device holder 20 illustrated herein, the engagement members 27 are externally threaded fasteners that are structured to threadably engage apertures in the front plate 22 of the housing 14. More particularly, the engagement members 27 are movable from a locked position wherein a compression force is applied to the sliding plate 17 to maintain its position relative to the front plate 22 of the housing 14, to an unlocked position wherein the compression force is released and the sliding plate 17 is movable relative to the front plate 22. Prior to commencing movement of the sliding plate 17, the engagement members 27 are first rotated in a counter-clockwise direction 51A as illustrated in FIG. 4A. Rotating the engagement members 27 in such a manner releases the compression force applied to the sliding plate 17. After releasing the compression force by moving the engagement members 27 from the locked to the unlocked position, the delivery device holder 20 may be slid to the position illustrated in FIG. 5 to substantially align the seat member 19 with the center axis of the access aperture 26. Once the seat member 19 has been properly aligned, the engagement members 27 may be rotated in a clockwise direction 51B as illustrated in FIG. 5 to prevent subsequent movement of the delivery device holder 20 relative to the front plate 22 of the housing 14.

Although movement of the delivery device holder 20 has been described as occurring after the compression assembly 12 has been actuated to the crimped position, those skilled in the art will appreciate that the seat member 19 may be aligned with the center axis of the access aperture 26 at any time without departing from the intended scope of the present disclosure. For example, the seat member 19 of the delivery device holder 20 may be aligned with the center axis of the access aperture 26 prior to actuating the actuation lever 16 to commence the crimping process.

FIGS. 6A-6D are perspective, side, top, and bottom views, respectively, of one of the bars 34 in accordance with the present disclosure. As illustrated in FIGS. 6A-6D, the bar 34 includes a proximal end 53, a distal end 55, a front face 70, a back face 72, a first side face 74, a second side face 76, and a chamfered leading edge 78. The first and second side faces 74 and 76 are substantially straight or planar surfaces that are generally parallel to one another. The second side face 76 opposes and intersects the chamfered leading edge 78 near the distal end 55. As further illustrated in FIGS. 6A-6D, a proximal portion of the bar 34 comprises a front leg 80A and a back leg 80B separated by a proximal opening 82 that is sized similar to or slightly larger than a width of the drive wheel 29. In the illustrated embodiment, the drive pin slot 40 extends through both the front leg 80A and the back leg 80B. However, in alternative embodiments, the drive pin slot 40 may extend completely through either the front leg 80A or the back leg 80B and only partially through the other of the front leg 80A or the back leg 80B as will be appreciated by those skilled in the art.

Although the distal end 55 is illustrated as comprising a substantially flat chamfered leading edge 78, the leading edge 78 may alternatively be structured with a non-flat, curvilinear, and/or rounded surface without departing from the intended scope of the present disclosure.

Figure 6A:
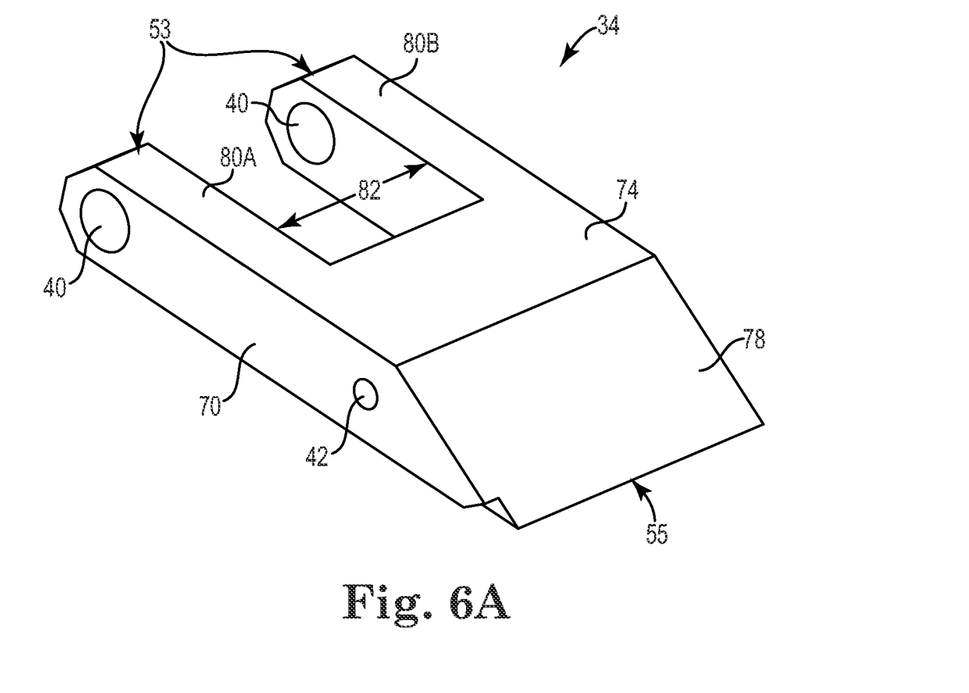
FIGS. 6A-6D are perspective, side, top, and bottom views, respectively, of a compression assembly bar in accordance with the present disclosure.
Figure 6B:
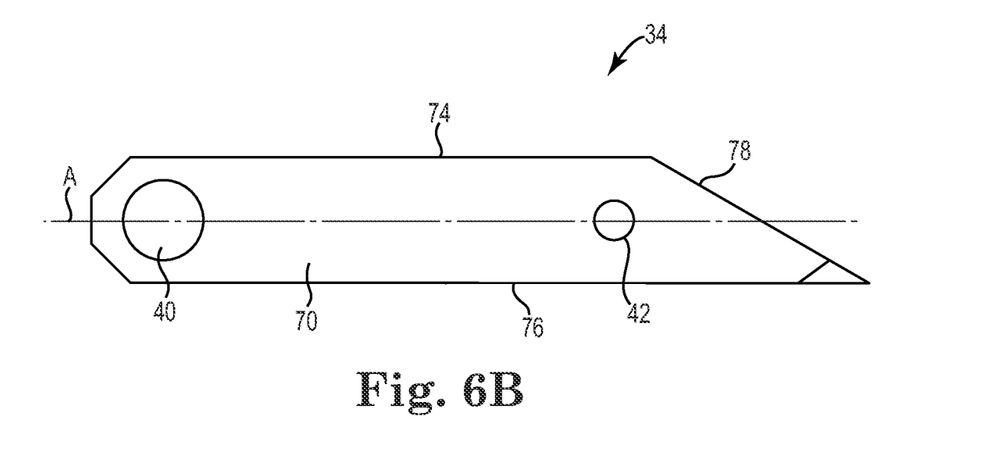
Figure 6C:
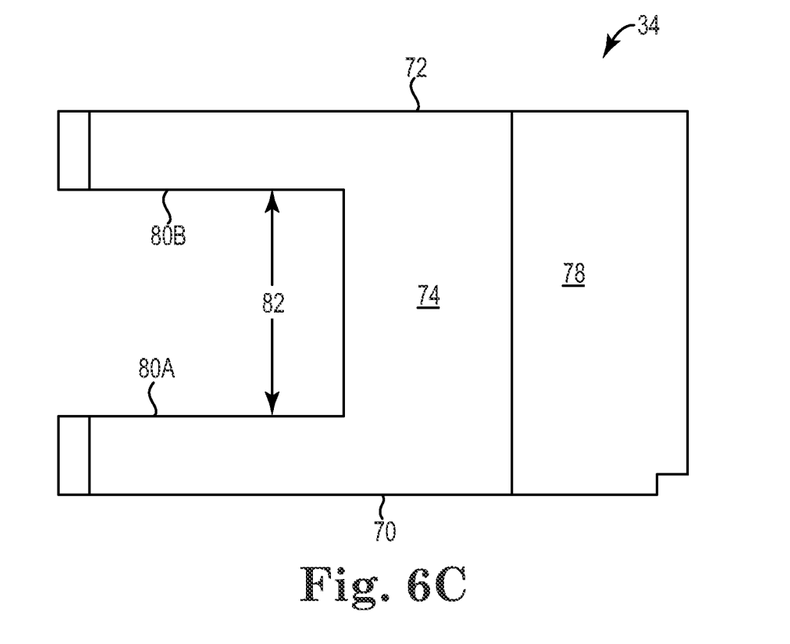
Figure 6D:
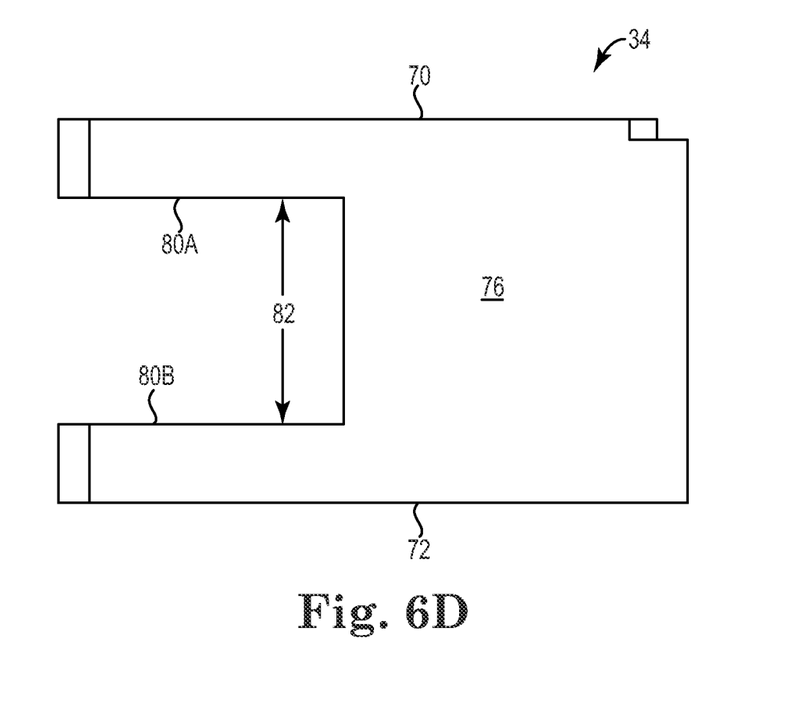

As illustrated in FIG. 6B, the centers of the drive pin slot 40 and the guide pin slot 42 are substantially aligned with a bar axis A extending through a center plane of the bar 34. However, in alternative embodiments, the drive pin slot 40 and/or the guide pin slot 42 may be offset from the bar axis A. As will be appreciated by those skilled in the art, offsetting the drive pin slot 40 and/or the guide pin slot 42 may provide additional tolerance for movement of the bars 34 through the crimping range of the compression assembly 12.

The bars 34 may be constructed using any suitable material as will be appreciated by those skilled in the art. Exemplary materials may include, but are not limited to, polymeric materials, polycarbonate materials, thermoplastic materials, ceramic materials, composite materials, metallic materials, and the like.

Figure 7:
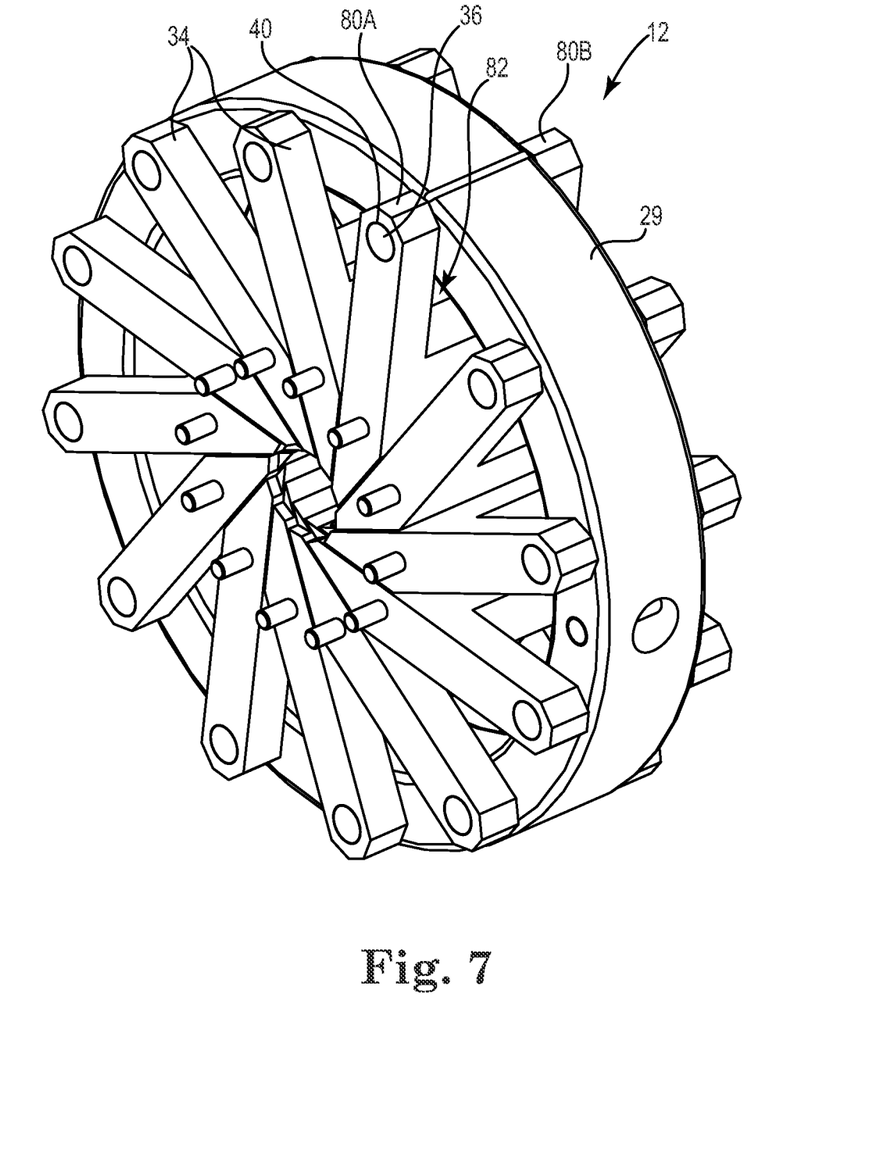
FIG. 7 is a perspective view of the compression assembly and attached drive wheel removed from the crimping tool.

FIG. 7 is a perspective view of the compression assembly 12 and the drive wheel 29 removed from the crimping tool to illustrate the positioning of the drive wheel 29 relative to the bars 34 of the compression assembly 12. As illustrated in FIG. 7, the drive wheel 29 is structured and sized to be positioned within the proximal opening 82 between the front leg 80A and the back leg 80B of the bars 34. As previously discussed, the compression assembly 12 is operably coupled to the drive wheel 29 by inserting the drive pin 36 through the drive pin slot 40 in the front and back legs 80A and 80B and the drive wheel slot 44 of the drive wheel 29 positioned therebetween.

Figure 8:
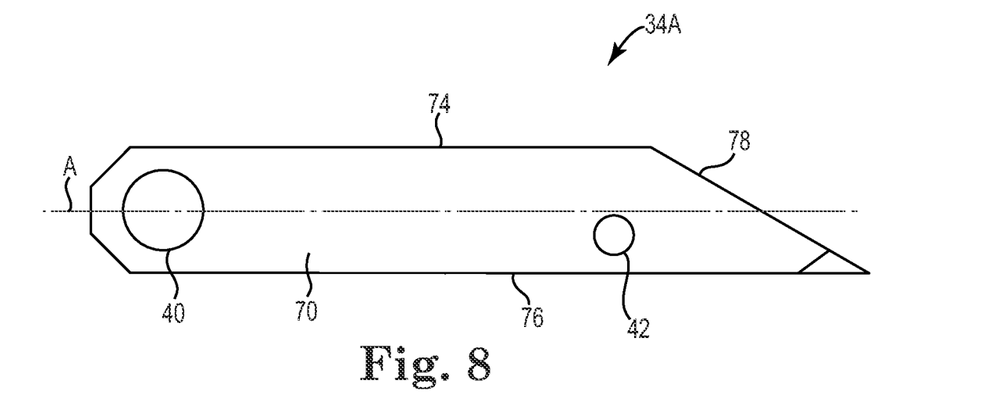
FIG. 8 is an alternative embodiment of a compression assembly bar in accordance with the present disclosure.

FIG. 8 is a side view of an alternative embodiment bar 34A in accordance with the present disclosure. As illustrated in FIG. 8, the bar 34A is substantially similar to the bar 34 previously described in detail with reference to FIGS. 6A-6D. However, instead of the drive pin slot 40 and the guide pin slot 42 of the bar 34A being in substantial alignment with the bar axis A, the guide pin slot 42 of the bar 34A is offset from the bar axis A. As will be appreciated by those skilled in the art, the guide pin slot 42 may be offset in either direction, i.e. toward the first side face 74 or the second side face 76, without departing from the intended scope of the present disclosure.

Figure 9:
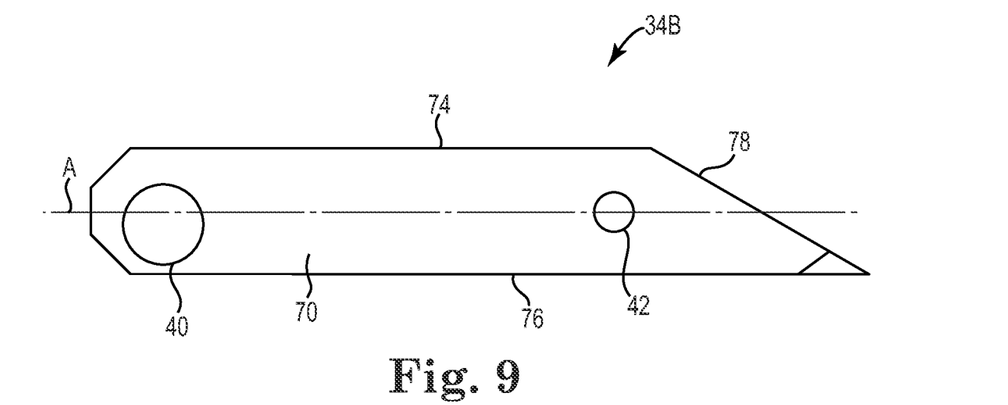
FIG. 9 is an alternative embodiment of a compression assembly bar in accordance with the present disclosure.

FIG. 9 is a side view of an alternative embodiment bar 34B in accordance with the present disclosure. As illustrated in FIG. 9, the bar 34B is substantially similar to the bar 34 previously described in detail with reference to FIGS. 6A-6D. However, instead of the drive pin slot 40 and the guide pin slot 42 of the bar 34B being in substantial alignment with the bar axis A, the drive pin slot 40 of the bar 34B is offset from the bar axis A. As will be appreciated by those skilled in the art, the drive pin slot 40 may be offset in either direction, i.e. toward the first side face 74 or the second side face 76, without departing from the intended scope of the present disclosure.

Figure 10:
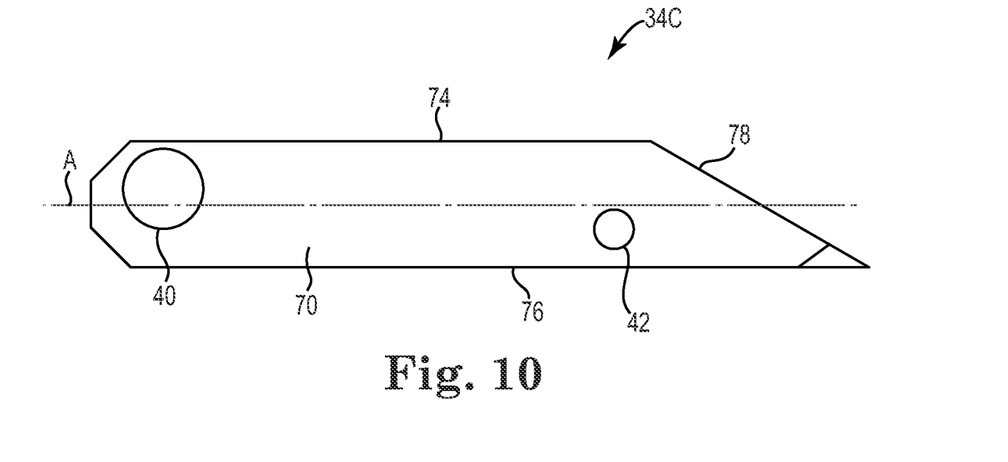
FIG. 10 is an exemplary alternative embodiment of a compression assembly bar in accordance with the present disclosure.

FIG. 10 is a side view of an alternative embodiment bar 34C in accordance with the present disclosure. As illustrated in FIG. 10, the bar 34C is a "hybrid" of the bar 34A of FIG. 8 and the bar 34B of FIG. 9 wherein both the drive pin slot 40 and the guide pin slot 42 are offset from the bar axis A. As will be appreciated by those skilled in the art, the drive pin slot 40 and the guide pin slot 42 may either be offset on opposite sides of the bar axis A or on the same side of the bar axis A without departing from the intended scope of the present disclosure.

Figure 11A:
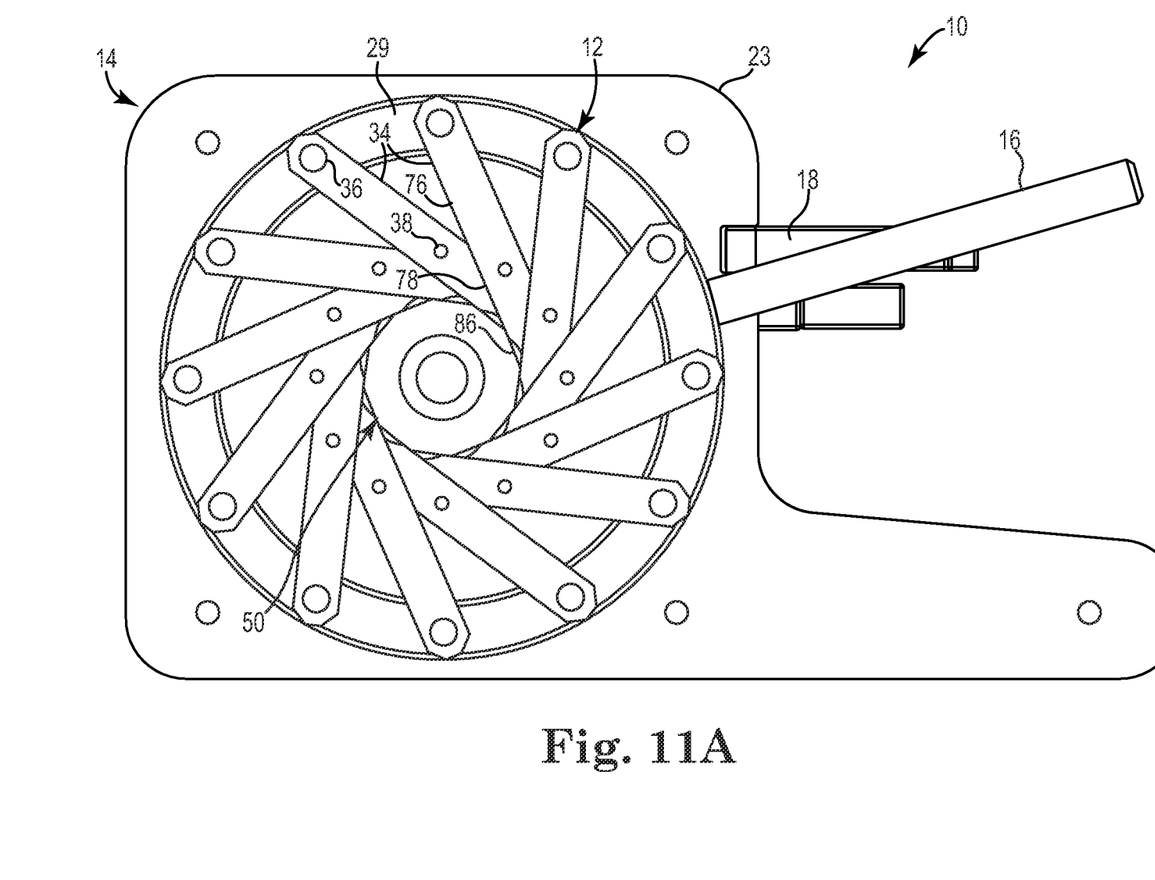
FIGS. 11A and 11B are front and back views, respectively, of the crimping tool of FIG. 1 with a front plate removed to illustrate movement of the compression assembly.

FIG. 11A is a front view of the crimping tool 10 with the front plate 22 (FIG. 2) removed illustrating the compression assembly 12 in the uncrimped position. As illustrated in FIG. 11A, the bars 34 are equally spaced around the drive wheel 29 and arranged such that the chamfered leading edge 78 of one bar 34 is slidable upon the second side face 76 of an adjacent bar 34 during the crimping process. Further, a perimeter of the chamber 50 is defined by an exposed portion 86 of the second side face 76 of each of the bars 34.

Figure 11B:
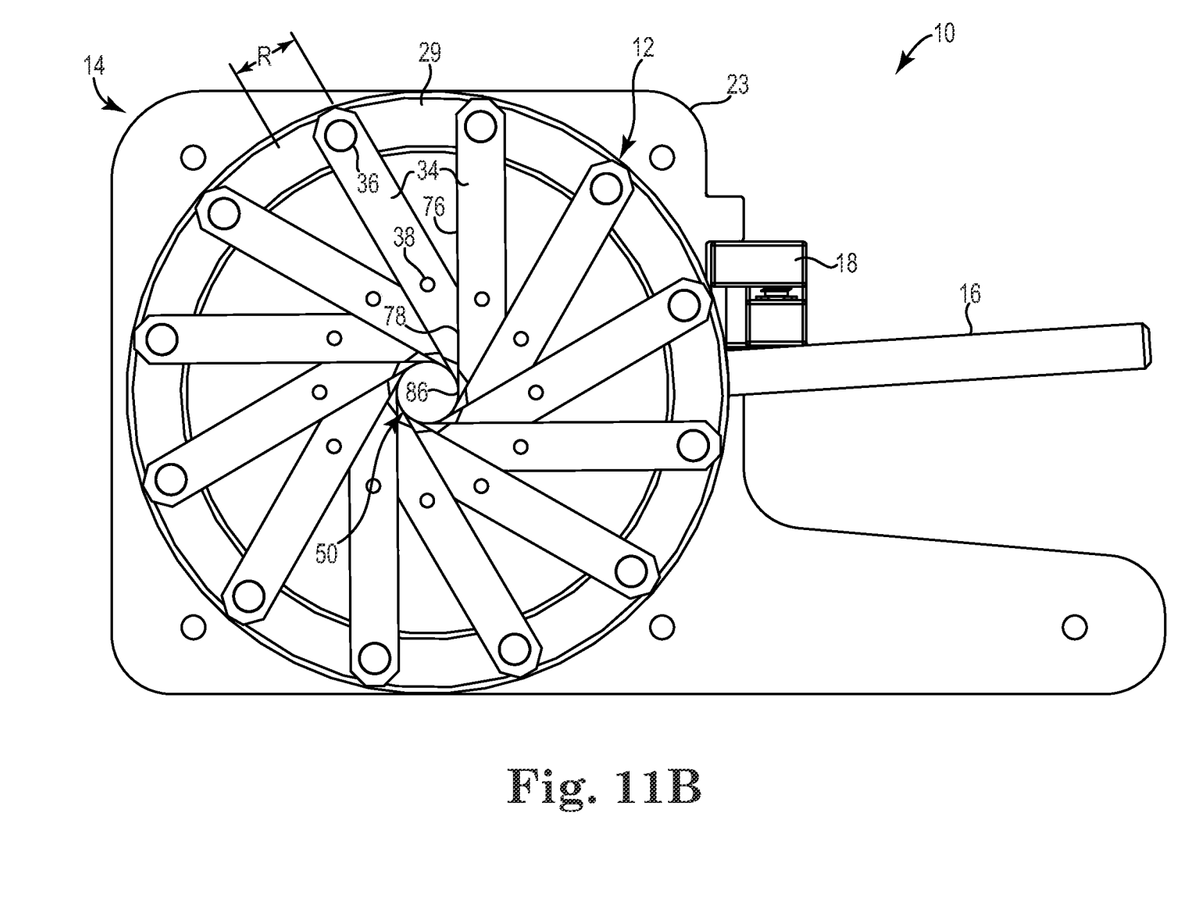

FIG. 11B is a front view of the crimping tool 10 with the front plate 22 (FIG. 2) removed illustrating the compression assembly 12 in the crimped position. As illustrated in FIG. 11B, the proximal ends of the bars 34 have rotated clockwise by a predetermined amount R relative to the uncrimped position. The distal ends of the bars 34 are constrained from any substantial amount of rotation due to the interaction of the guide pins 38 with the elongate slots 52 in the front plate 22 and the elongate slots 54 in the back plate 23 as previously discussed. Thus, the distal ends of the bars 34 are guided radially inward along the elongate guide slots 52 and 54 as the chamber 50 is contracted. As will be appreciated by those skilled in the art, in the crimped position illustrated in FIG. 11B there is a decrease in the size of the chamber 50 perimeter due to a reduction in the exposed portion 86 of the second side face 76 of each of the bars 34.

The compression assembly 12 is described and illustrated herein as including twelve bars 34. However, the number of bars 34 may be varied as will be appreciated by those skilled in the art. For example, the requisite number of bars 34 may depend upon a diameter of the drive wheel 29 or a width of the bars 34 between the first side face 74 and the second side face 76. Thus, twelve bars 34 are illustrated merely for purposes of example and not limitation.

Although the present disclosure has been described with reference to preferred embodiments, workers skilled in the art will recognize that changes can be made in form and detail without departing from the spirit and scope of the present disclosure.

What is claimed is:

1. A crimping tool comprising:
a housing having a front wall and a back wall;
a drive wheel movably positioned within the housing, the drive wheel including an actuation lever for moving the wheel between a first position and a second position;
a plurality of bars operably coupled to the drive wheel and having a proximal end and a distal end, the distal end of the bars including a chamfered leading edge and an opposing planar surface and the proximal end of the bars including first and second legs forming a proximal opening therebetween;
a chamber defined by the planar surfaces at the distal ends of the bars, the chamber being reducible in size from a first enlarged size to a second reduced size as the actuation lever moves from the first position to the second position; and
a delivery device holder mounted on the front wall, the delivery device holder comprising a sliding plate slidably coupled to the front wall via at least one engagement member that extends from the front wall through a corresponding horizontal slot of the sliding plate.

2. The crimping tool of claim 1, wherein the chamfered leading edge of each of the bars lies adjacent to the planar surface of an adjacent bar.

3. The crimping tool of claim 2, wherein the drive wheel is positioned within the proximal openings of the bars.

4. The crimping tool of claim 3, wherein each of the bars includes a drive pin slot and a guide pin slot.

5. The crimping tool of claim 4, wherein the drive wheel includes a plurality of drive wheel slots, the drive wheel operably coupled to the bars with a plurality of drive pins extending between the drive pin slots in the bars and the drive wheel slots.

6. The crimping tool of claim 5 further comprising:
a first plurality of radially extending slots in the front wall; and
a second plurality of radially extending slots in the back wall;
wherein each of the bars is operably coupled to the housing with a guide pin extending through the guide pin slot and into a corresponding one of the radially extending slots in the front wall and the back wall.

7. The crimping tool of claim 6, wherein the drive pin slot and the guide pin slot are positioned along an axis extending through a center plane of the bar.

8. The crimping tool of claim 1, wherein the delivery device holder comprises a seat member structured to receive a delivery device.

9. The crimping tool of claim 8, wherein the delivery device holder is slidable between a first position and a second position, the seat member being substantially aligned with a center axis of the chamber in the second position.

10. The crimping tool of claim 1, wherein the at least one delivery device holder engagement member is movable between a first position in which the delivery device holder is slidable relative to the front wall and a second position in which the delivery device holder is fixed relative to the front wall.

* * * * *